United States Patent [19]

Nishio et al.

[11] Patent Number: 5,033,841
[45] Date of Patent: Jul. 23, 1991

[54] OPHTHALMOLOGICAL INSTRUMENT

[75] Inventors: Kouji Nishio; Hiroshi Iijima; Kenjiro Katsuragi; Yoshihiko Hanamura, all of Tokyo, Japan

[73] Assignee: Kabushiki Kaisha Topcon, Tokyo, Japan

[21] Appl. No.: 429,290

[22] Filed: Oct. 31, 1989

[30] Foreign Application Priority Data

Nov. 1, 1988 [JP] Japan .................................. 63-276968
Nov. 1, 1988 [JP] Japan .................................. 63-276971
Nov. 8, 1988 [JP] Japan .................................. 63-281598

[51] Int. Cl.$^5$ ............................ A61B 3/10; A61B 3/16
[52] U.S. Cl. ..................................... 351/212; 351/247; 128/645
[58] Field of Search ................. 351/212, 247, 208; 128/645, 648, 652

[56] References Cited

U.S. PATENT DOCUMENTS 4,710,003 12/1987 Masuda .............................. 351/212

Primary Examiner—Rodney B. Bovernick
Attorney, Agent, or Firm—Finnegan, Henderson, Farabow, Garrett & Dunner

[57] ABSTRACT

An ophthalmological instrument for the use of both corneal configuration and intraocular pressure measurement has alignment watching means for watching an alignment completion state upon receipt of an alignment completion signal which is output by alignment detecting means for detecting the alignment of an apparatus body with respect to an eye to be tested, corneal configuration measuring means for projecting a ring target mark onto the cornea of the eye and measuring a corneal configuration with reference to the ring target image, noncontact type intraocular pressure measuring means for discharging fluid toward the cornea in order to transfigure the cornea and measuring the intraocular pressure with reference to the amount of such transfiguration, and automatic executing means for executing the corneal configuration and intraocular pressure measurements in such a manner as that data of the ring target image is intaken in accordance with output of the alignment watching means in order to obtain data regarding the corneal configuration and thereafter checking whether the alignment completion state is maintained and if affirmative, automatically starting a fluid discharge onto the cornea.

3 Claims, 15 Drawing Sheets

OPHTHALMOLOGICAL INSTRUMENT

FIELD OF THE INVENTION

This invention relates to an ophthalmological instrument capable of measuring intraocular pressure of an eye to be tested and the configuration of the cornea of the eye in a noncontact manner, and more particularly to an ophthalmological instrument capable of measuring the intraocular pressure and the configuration of the cornea with ease.

PRIOR ART

As means for measuring intraocular pressure of an eye to be tested in a noncontact manner, there is a tonometer as disclosed in, for example, Japanese Patent Publication No. Sho 54-38437, Japanese Patent Application No. Sho 59-242279 or Japanese Patent Publication No. Sho 62-30768.

The device of Japanese Patent Publication No. Sho 54-38437 is designed as such that an air pulse as a fluid is discharged toward the cornea of an eye to be tested in accordance with a known pressure-time function and the applanation state of the cornea is photoelectrically detected to measure a period of time from the start of discharging an air pulse (sometimes referred to as "air puff") to the applanation of the cornea in order to measure intraocular pressure of the eye.

Also, the device of Japanese Patent Application No. Sho 59-242279 is designed as such that an air pulse is discharged to the cornea of the eye to detect pressure of the discharging air pulse, a reflected light quantity from the cornea is photoelectrically detected with reference to the pressure as a parameter and intraocular pressure is measured from such detected air pulse when the cornea is transfigured by a predetermined amount.

Furthermore, the device of Japanese Patent Publication No. Sho 62-30768 is designed as such that an air current of a predetermined pressure is discharged to the cornea, a light flux is irradiated to the cornea, and intraocular pressure is measured in accordance with varied quantity of the light flux reflected by the cornea before and after the air current is discharged to the cornea.

On the other hand, as means for measuring the radius of curvature of the cornea of the eye to be tested, corneal configuration measuring devices disclosed in Japanese Patent Application No. Sho 61-102800 and Japanese Patent Application No. Sho 61-310009 are known. The devices disclosed in these publications are designed as such that a ring pattern (kerato ring image) is projected to the cornea of the eye through an objective lens facing the eye, an image thereof reflected by the cornea is received by a two-dimensional detecting element such as an area CCD, and the radius of curvature of the cornea, etc. are measured from the configuration of the pattern.

As seen in the above, heretofore, the measurement of intraocular pressure of the eye and the measurement of the radius of curvature are separately effected using separate devices such as a noncontact type tonometer (hereinafter referred to as the "tonometer") and a corneal configuration measuring device (hereinafter referred to as the "keratometer").

PROBLEM TO BE SOLVED BY THE INVENTION

However, both the tonometer and keratometer require an alignment between the eye and the device body in order to carry out the respective measurements. As a long period of time and training are required for performing this alignment operation, it takes much time for carrying out the eye inspection in a case that the eye inspection requires both type of the measurements. Therefore, burdens of time are increased for both the inspector and the person to be inspected. Also, in spectacle shops, ophthalmic hospitals and the like, they purchase tonometers and keratometers separately and place those equipment in an eye examination room and an eye inspection room for the above-mentioned purpose. This becomes not only a burden in respect of expense but also a burden in respect of securing a space for eye inspection.

Therefore, regarding the measurement of the intraocular pressure and corneal configuration, it is demanded an ophthalmological instrument for the use of both corneal configuration measurement and intraocular pressure measurement which can realize shortening of the time for eye testing, reduction of time and labor, saving of space, and low costs. In this case, if the alignment must be verified every time the corneal configuration and the intraocular pressure are measured, much time and labor are required.

The present invention was accomplished in view of the above-mentioned problems. It is therefore the object of the present invention to provide an ophthalmological instrument which is capable of simplifying the alignment operation and shortening a whole period of time required for the use of both corneal configuration measurement and intraocular pressure measurement.

MEANS FOR SOLVING THE PROBLEM

In order to achieve the above-mentioned object, an ophthalmological instrument of the present invention includes:

alignment watching means for watching an alignment completion state upon receipt of an alignment completion signal which is output by alignment detecting means for detecting the alignment of an apparatus body with respect to an eye to be tested;

corneal configuration measuring means for projecting a ring target mark onto the cornea of the eye and measuring a corneal configuration with reference to said ring target image;

noncontact type intraocular pressure measuring means for discharging fluid toward the cornea in order to transfigure the cornea and measuring the intraocular pressure with reference to the amount of such transfiguration; and automatic executing means for executing the corneal configuration and intraocular pressure measurements in such a manner as that data of the ring target image is intaken in accordance with output of said alignment watching means in order to obtain data of the corneal configuration and thereafter checking whether the alignment completion state is maintained and if affirmative, automatically starting a fluid discharge onto the cornea.

According to the ophthalmological instrument as claimed the present invention, the alignment watching means watches whether the alignment completion state is maintained upon receipt of the alignment completion signal. And when the alignment watching means confirms that the alignment completion state is maintained for a certain period of time, it outputs a command signal to the automatic executing means and the automatic executing means automatically intakes the data of the corneal configuration.

The watching means watches whether the alignment completion state is maintained after the ring target image is projected and if affirmative, starts discharging the fluid toward the cornea in order to obtain the intraocular pressure.

According to the ophthalmological instrument as claimed in the present invention, both the corneal configuration and intraocular pressure measurements can automatically be performed by a single alignment operation when both the corneal configuration and intraocular pressure measurements are to be performed using a single ophthalmological instrument. Accordingly, the time for measurement by alignment operation can be shortened. Also, the present invention is constructed such that measuring data of the corneal configuration is intaken and thereafter, measuring data of the intraocular pressure is intaken. Accordingly, this invention is convenient. Such an inconvenience as the operator waiting until the transfigured cornea returns to its original state when the intraocular pressure is measured first and thereafter the corneal configuration is measured can be avoided.

Furthermore, it is checked whether the alignment completion state is maintained even after the corneal configuration is measured and the intraocular pressure measured data is obtained. Accordingly, it can be expected that such obtained intraocular pressure is accurate.

In order to achieve the above object, an ophthalmological instrument of the present invention includes:

alignment detecting means for detecting the alignment of an apparatus body with respect to an eye to be tested;

corneal configuration measuring means for automatically projecting a ring target mark of the cornea of the eye in accordance with an alignment completion output of said alignment completion detecting means and calculating means to measure the radius of curvature of the cornea with reference to the ring target image formed on the cornea;

data check means for checking whether data of the radius of curvature of the cornea is obtained; and noncontact type intraocular pressure measuring means for discharging fluid toward the cornea in order to transfigure the cornea and measuring the intraocular pressure with reference to the amount of such transfiguration under the conditions that the alignment completion state is still maintained and that the data regarding the radius of curvature is obtained based on said data check means and said alignment detecting means.

According to the ophthalmological instrument of the present invention, the corneal configuration measuring means automatically projects the ring target mark onto the cornea of the eye in accordance with the alignment completion output of the alignment detecting means and calculating means to measure the radius of curvature of the cornea with reference to the ring target image formed on the cornea. The data check means checks whether the data regarding the radius of curvature of the cornea is obtained. The intraocular pressure measuring means discharges fluid toward the cornea and measures the intraocular pressure under the conditions that the data regarding the radius of curvature of the cornea is obtained and that the alignment completion state is still maintained based on the data check means and the alignment detecting means.

According to the ophthalmological instrument as claimed in the present invention, the construction is such that after the data regarding the radius of curvature of the cornea is obtained, it is checked that the data of the radius of curvature of the cornea is obtained and it is also checked that the alignment is already completed, and thereafter it automatically goes to the intraocular measurement. Accordingly, the operator can devote himself to the intraocular measurement without having an uneasy feeling about whether the data of the corneal configuration is obtained. In addition, it can be expected that such obtained intraocular pressure is accurate.

In order to achieve the above object, an ophthalmological instrument according to the present invention includes:

an alignment detecting system for aligning an optical axis with the vertex of the cornea of an eye to be tested and detecting the amount of working distance;

a noncontact type intraocular pressure measuring system;

a corneal configuration measuring system for projecting a predetermined target mark onto the cornea of the eye, permitting a light receiving element to receive a kerato ring image of the target mark, and performing a calculation with reference to the configuration of the kerato ring image thereby to measure the radius of curvature of the cornea; and correcting means for performing correction with reference to the amount of the working distance which is detected by said alignment detecting system when the corneal configuration is being calculated by said corneal configuration measuring system.

The ophthalmological instrument as claimed in the present invention is constructed such that in the alignment detecting system, after the optical axis of the ophthalmological instruments aligned with the vertex of the cornea of the eye and the working distance is adjusted, the intraocular pressure and the corneal configuration of the eye are measured by the intraocular pressure measuring system and the corneal configuration measuring system.

In the corneal configuration measuring system, the radius of curvature of the cornea is measured with reference to the configuration of the kerato ring image, working distance, etc. However, in the state where the alignment is already verified, errors are sometimes occurred in working distance. If the errors occurred in working distance, errors would occur in the radius data of the curvature of the cornea. Therefore, the errors are corrected by this correcting means and the radius of curvature of the cornea is calculated by the corneal configuration measuring system so as to measure a proper corneal configuration.

As the value of the working distance can be corrected by providing this correcting means, there can be exhibited such a practically very useful effect as that a proper corneal configuration can be measured.

BRIEF DESCRIPTION OF THE DRAWINGS

FIG. 16 is a schematic view showing the imaging state on the position sensor;

FIG. 17 is an electric circuit diagram showing the position sensor and the control circuit, etc.;

FIGS. 18(a) through 18(f) are schematic views showing the imaging state of the position sensor;

FIG. 19 is a plan view showing the projecting state of an alignment target ray toward the cornea; and FIG. 20 is a perspective view showing the imaging state to the position sensor.

EMBODIMENT

The embodiments of an ophthalmological instrument according to the present invention will be described hereinafter with reference to the accompanying drawings.

Figure 4:
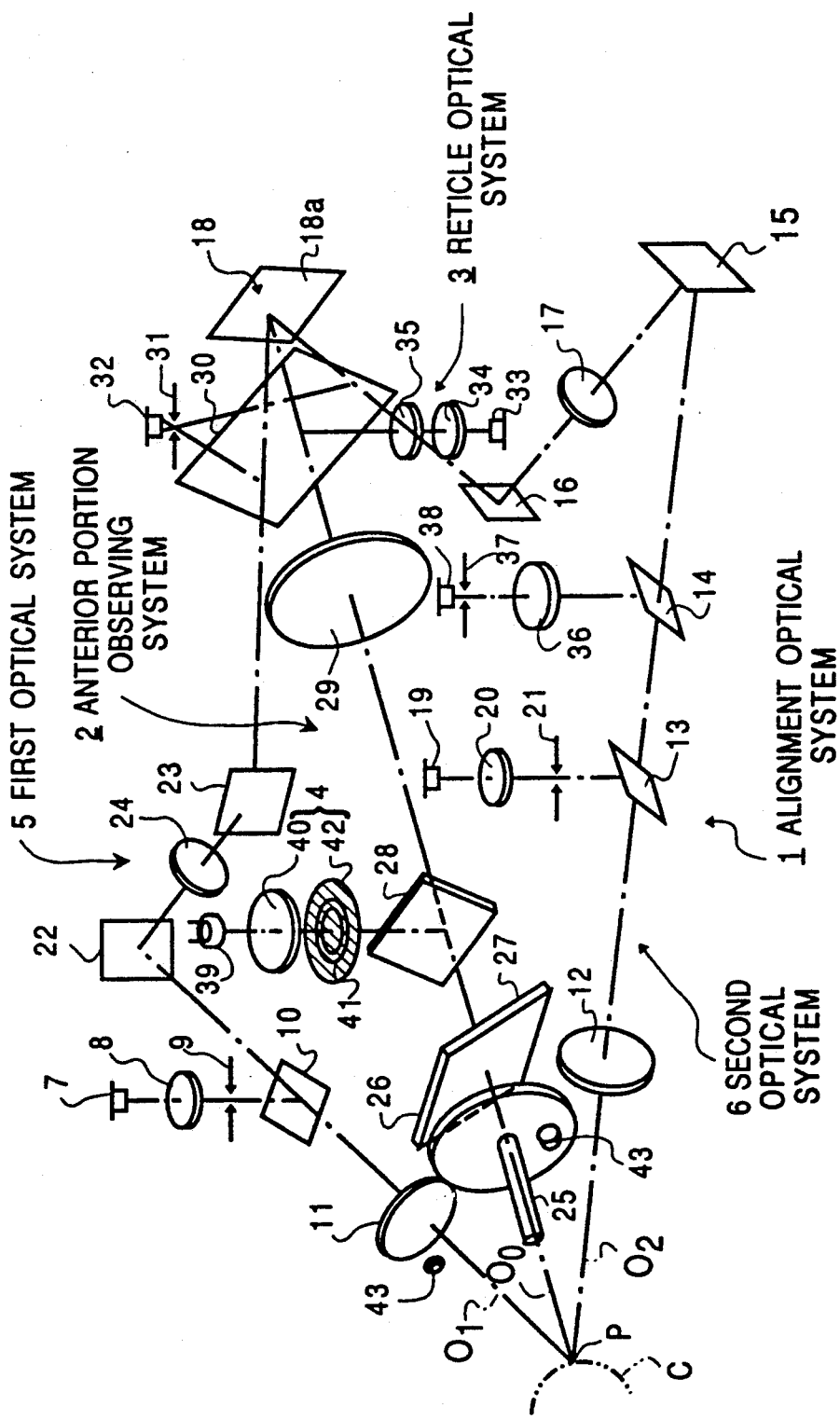
FIG. 4 is a perspective view of an optical system of the ophthalmological instrument according to the present invention.

FIG. 4 shows a perspective view of an optical system of an ophthalmological instrument according to the present invention. This optical system generally comprises an alignment optical system 1, an anterior portion observing system 2, a reticle optical system 3, and a ring target image projecting system 4.

Figure 5:
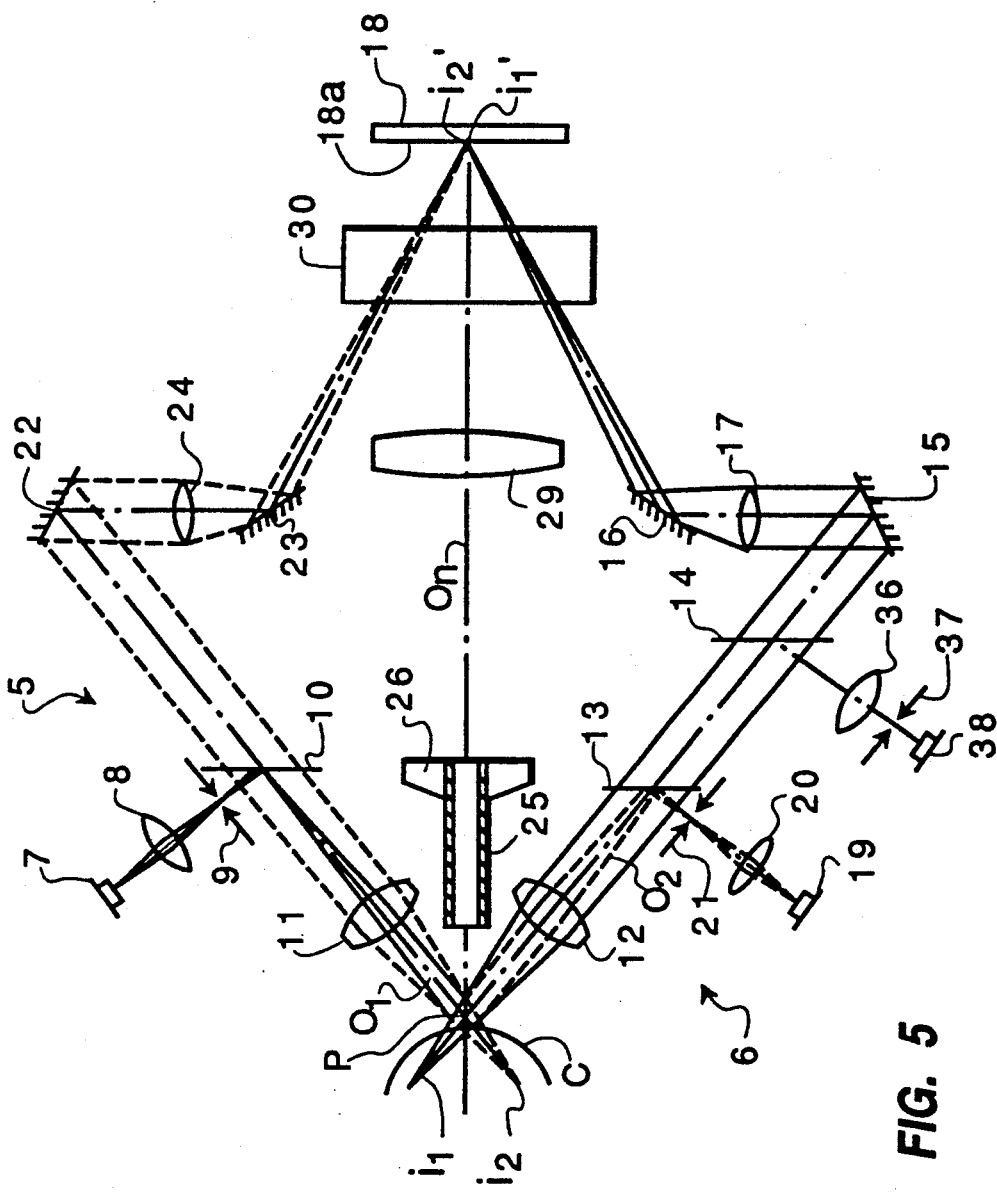
FIG. 5 is an optical diagram for explaining the operation of an alignment optical system.

The alignment optical system 1, as shown in FIGS. 4 and 5, includes a first optical system 5 and a second optical system 6. The first optical system 5 has an LED 7 as a light source. The LED 7 irradiates an infrared light of, for example, 760 nm (shown by the solid line in FIG. 5). The infrared light of a wavelength of 760 nm is condensed by a condenser lens 8. Thereafter, the infrared light passes through an aperture of a diaphragm 9 as an alignment target mark. And the infrared light passed through the aperture of the diaphragm 9 is reflected by an infrared dichroic mirror 10 and guided to a projection lens 11. The projection lens 11 has a focal point in the position of the aperture of the diaphragm 9.

The infrared light of the LED 7 is made into a parallel pencil of rays by the projecting lens 11. The parallel pencil of rays are projected to the cornea C of an eye to be tested as an alignment target light of the cornea C. A virtual image $i_1$ as a target image is formed on the cornea C by the alignment target light reflected on the cornea C.

The second optical system 6 has a projection lens 12, an infrared dichroic mirror 13, a half mirror 14, mirrors 15, 16, and an imaging lens 17. The reflected light forming the virtual image $i_1$ passes the projection lens 12 of the second optical system 6 and becomes a parallel pencil of rays.

The parallel pencil of rays pass the infrared dichroic mirror 13 and the half mirror 14 and are then guided to the imaging lens 17 disposed between the mirrors 15 and 16. The parallel pencil of rays guided to the imaging lens 17 are imaged on a light receiving surface 18a of an area 18 which forms a part of the anterior portion observing system 2 by the imaging lens 17 as an alignment target image $i_1'$.

Also, the second optical system 6 is provided with an LED 19. The LED 19 irradiates an infrared light of a wavelength of, for example, 860 nm. The infrared light of a wavelength of 860 nm is condensed by a condenser lens 20. Thereafter, the infrared light is allowed to pass through an aperture of a diaphragm 21 as an alignment target mark, reflected by an infrared dichroic mirror 13 and guided to a projection lens 12. The projection lens 12 has a focal point in the position of the aperture of the diaphragm 21. The infrared light of the LED 19 (shown by the broken line in FIG. 5) is made into a parallel pencil of rays by the projecting lens 12.

And the parallel pencil of rays are projected onto the cornea C of the eye as an alignment target light. A virtual image $i_2$ as an alignment target image is formed on the cornea C of the eye. The first optical system 5 is provided with mirrors 22, 23, and an imaging lens 24.

The reflected light forming the virtual image $i_2$ becomes a parallel pencil of rays after passed through the projection lens 11 of the first optical system 5. After passed through the projection lens 11 of the first optical system 5, the parallel pencil of rays are guided to an imaging lens 24 between the mirrors 22 and 23. The parallel pencil of rays guided to the imaging lens 24 are imaged on a light receiving surface 18a of the area CCD 18 as an alignment target image $i_2'$ by the imaging lens 24.

The anterior portion observing system 2 includes a fluid discharge nozzle 25, an objective lens 26, a glass plate 27, a half mirror 28, an imaging lens 29, and a visible light transmitting and infrared light reflecting type dichroic mirror 30. When the intersecting point of the respective optical axes $O_1$, $O_2$ (see FIG. 5) of the first and the second optical systems 5 and 6 and the alignment axis On of the air pulse discharge nozzle 25 is brought to be coincident with the vertex P of the cornea C, the virtual images $i_1$ and $i_2$ are present on $O_1$ and $O_2$ and on the focal surface of the cornea C, and the target images $i_1'$ and $i_2'$ are brought to be coincident with each other on the light receiving surface 18a of the CCD 18.

At this time, a correct alignment between a regular reference operation distance and the eye can be obtained. The imaged light by the imaging lenses 17 and 24 is reflected by a dichroic mirror 30 and made incident to an alignment sensor 32 as an alignment detecting means through a diaphragm 31.

The reticle optical system 3 generally comprises a light source 33, a reticle plate 34, and an imaging lens 35. The light source 33 emits an infrared light. The infrared light emitted from the light source 33 illuminates the reticle plate 34. The illumination light, which has passed through the reticle plate 34, is guided to the imaging lens 35. The illumination light guided to the imaging lens 35 is reflected by the dichroic mirror 30 and guided to the CCD 18. This illumination light is imaged on the CCD 18 as a circular reticle image 34a (see FIGS. 11a and 11b) by the imaging lens 35.

The alignment optical system 1 is commonly used means for detecting applanation of the cornea in this embodiment. As the means for detecting applanation of the cornea, there are used the LED 7, the condenser lens 8, the opening of the diaphragm 9, the infrared light reflecting dichroic mirror 10, and the projecting lens 11 of the first optical system 5, and the projecting lens 12, the infrared dichroic mirror 13, the half mirror 14, the imaging lens 33, the diaphragm 37, and the applanation sensor 38 of the second optical system 6.

Figure 6:
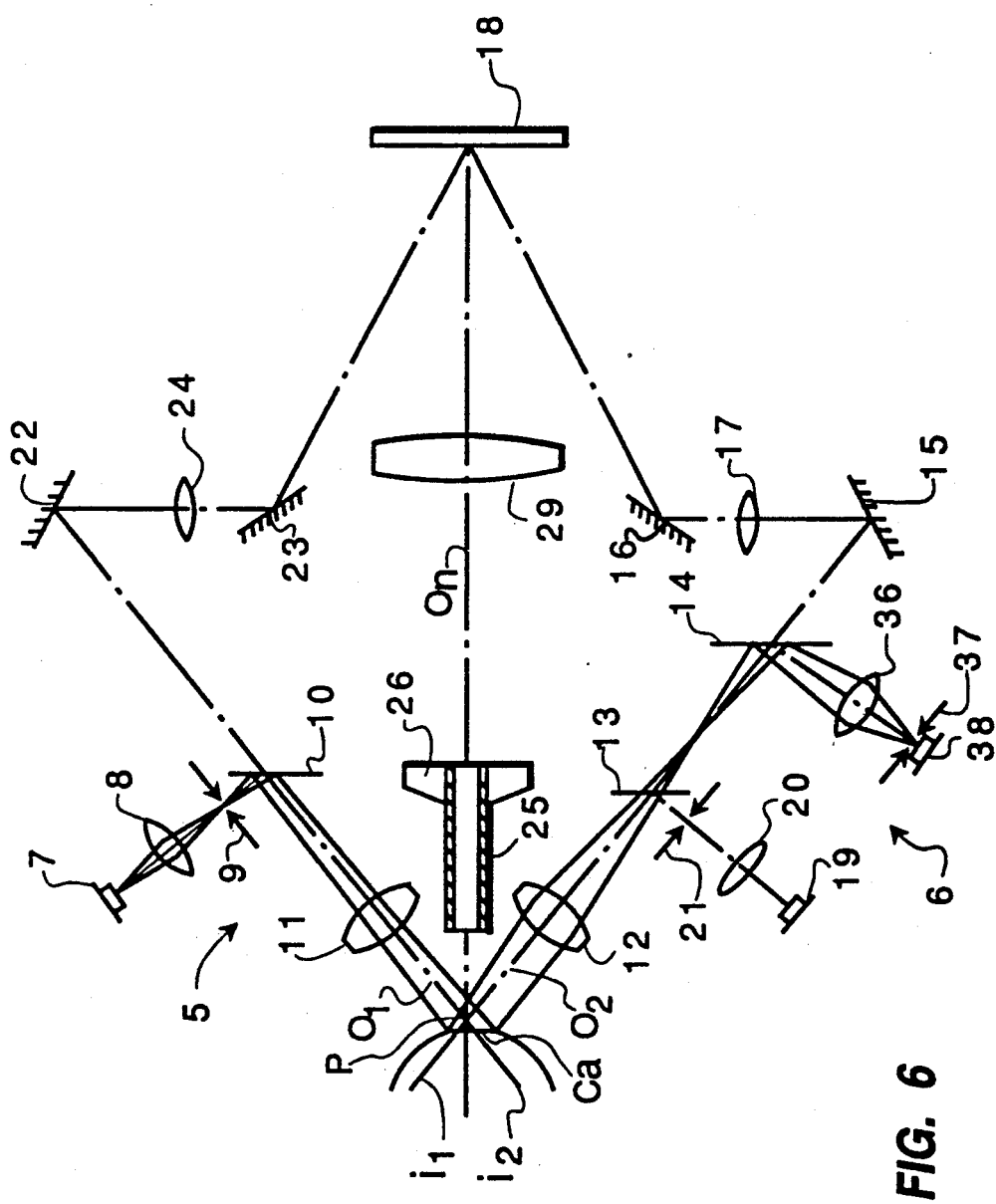
FIG. 6 is an optical diagram for explaining the operation for detecting applanation.

As is shown in FIG. 6, when an air pulse is discharged from the air puff discharge nozzle 25 to the cornea C and the cornea C is made applanation, the infrared light emitted from the projecting lens 11 of the first optical system 5 is reflected by the applanation cornea Ca while maintaining its form of the parallel pencil of rays. And this infrared light is made incident to the projecting lens 12 of the second optical system 6 and allowed to transmit through the infrared light dichroic mirror 13. Thereafter, the infrared light is guided to the half mirror 14, reflected by the half mirror 14 and then imaged on an opening of the diaphragm 37 by an imaging lens 36. The light receiving quantity of the applanation sensor 38 becomes maximum when the cornea is made applanation.

Figure 7:
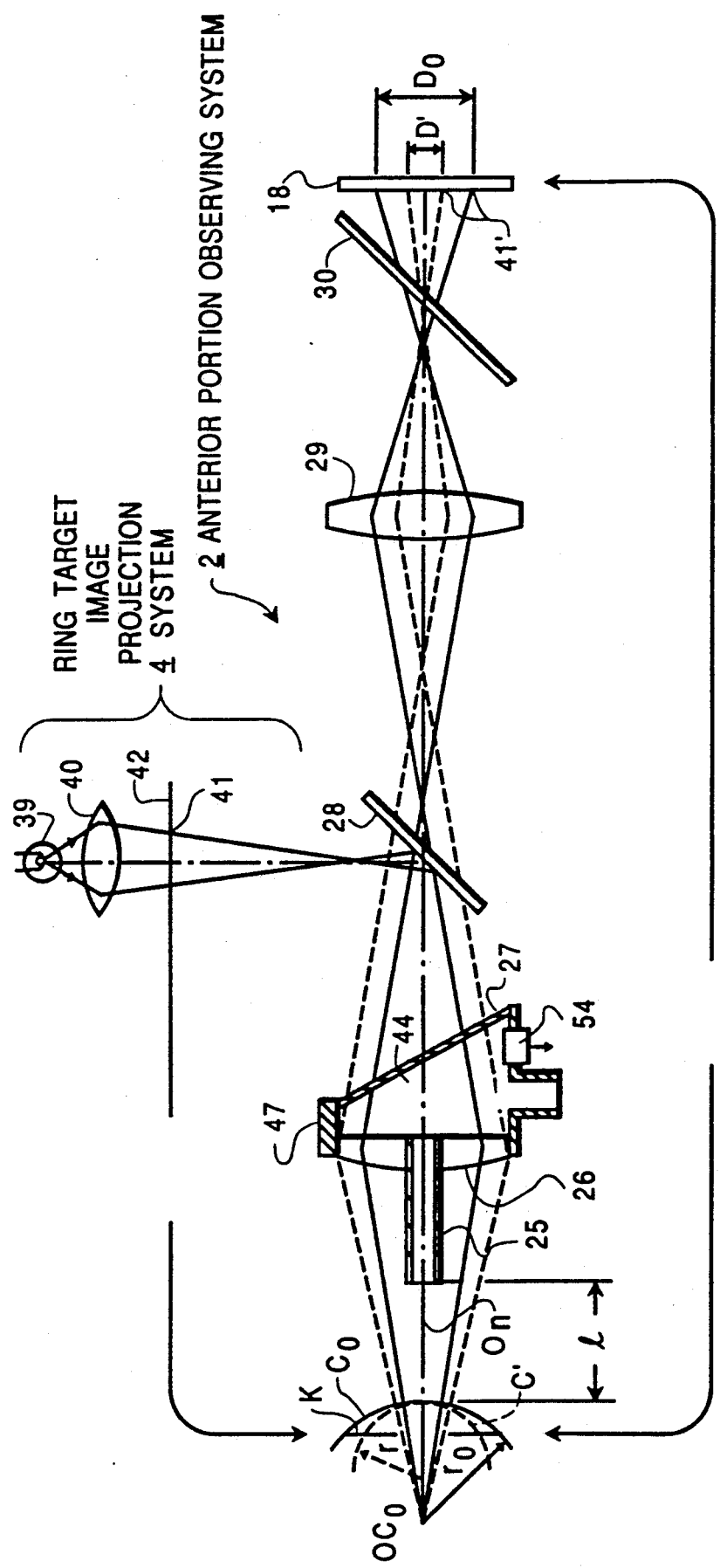
FIG. 7 is an optical diagram for explaining the operation for measuring a corneal configuration.

The anterior portion observing system 2 is commonly used in the optical system of the corneal configuration measuring means in this embodiment. The ring target image projecting system 4 functions as the optical system of the corneal configuration measuring means. The ring target image projecting system 4, as shown in FIG. 7, comprises a light source 39, a condenser lens 40, a pattern plate 42 having a ringshaped pattern 41 formed thereon. The light source 39 emits a visible light. The visible light emitted from the light source 39 is condensed by the condenser lens 40 and illuminates the ring-shaped pattern 41. After the light flux, which has transmitted through the ring-shaped pattern 41 is reflected by the half mirror 28, it is projected toward the cornea C by the objective lens 26. The objective lens 26 is constructed such that the ring-shaped pattern 41 is imaged generally in a position where the iris K is present.

The objective lens 26 and the imaging lens 29 are cooperatively worked to image the anterior portion including the iris K of the eye on the area CCD 18 as an anterior portion image, and the anterior portion is illuminated by visible light sources 43, 43.

The light flux, which has passed through the ring-shaped pattern 41, is projected in such a manner as to be condensed to the center of curvature $OC_0$ of a reference cornea $C_0$. The light flux reflected by the reference cornea $C_0$ is formed on the light receiving surface 18a of the CCD 18 by the objective lens 26 and the imaging lens 29. In this embodiment, the objective lens 26 and the imaging lens 29 are arranged in such a manner as that the image of the ring-shaped pattern 41 formed in the position of the iris K would be optically conjugate with the CCD 18. When the cornea $C_0$ has the radius of curvature $r_0$, if the cornea $C_0$ has no astigmatism, the corneal reflected pattern image 41' to be imaged on the CCD 18 is projected as a ring image of the diameter $D_0$.

When the cornea C' has the radius of curvature r' ($r' < r_0$), the corneal reflected image 41' of the ring-shaped pattern 41 is projected as a ring-shaped image having the diameter D'.

Therefore, by measuring the size of the pattern image 41' projected on the CCD 18, the radius of curvature of the cornea C can be measured. Also, when the cornea C has astigmatism, the reflected image 41' becomes elliptical. By measuring its long diameter and its short diameter, the radius of curvature in both strong and weak primary meridians of the cornea C can be known. Furthermore, the axial direction of astigmatism can be known from the direction of the long or short diameter.

The fluid discharge nozzle 26 forms a part of intraocular pressure measuring means adapted to measure the anterior pressure of the eye by discharging fluid toward the cornea C to transfigure the cornea C.

Figure 8:
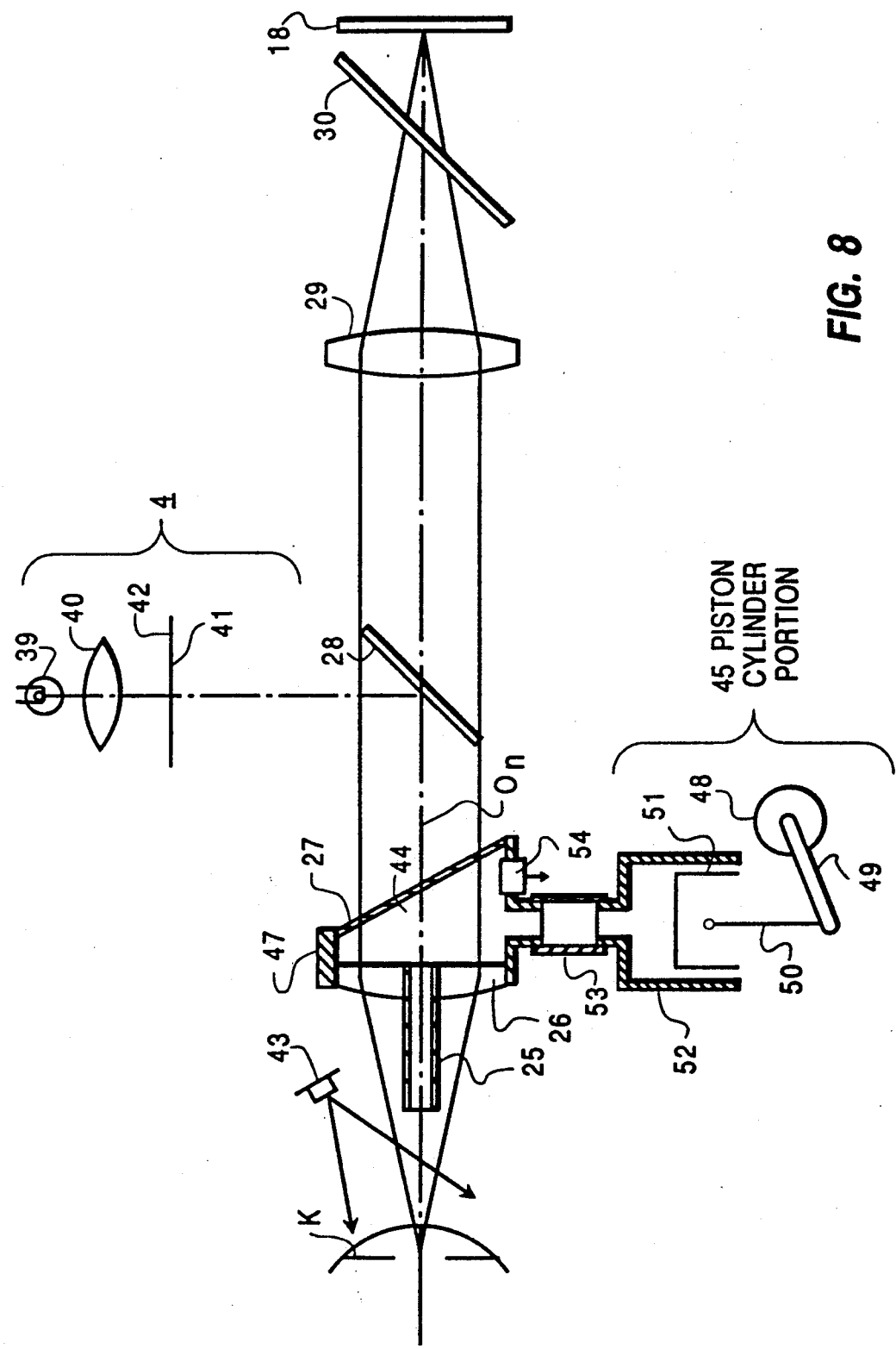
FIG. 8 is a schematic view showing the operation of the anterior portion observation and the constitution of a fluid discharge system.

The fluid discharge nozzle 25 is coaxially arranged with the alignment axial line On coaxial with the optical axis of the objective lens 26. In this embodiment, the fluid discharge nozzle 25 penetrates the central portion of the objective lens 26 and is mounted to the objective lens 26. The intraocular pressure measuring means includes a fluid discharge system 46. This fluid discharge system 46, as shown in FIG. 8, generally comprises a chamber 44, and a piston cylinder portion 45.

The chamber 44 is defined and sealed by the objective lens 26, the glass plate 27 and a cylindrical body 47. The piston cylinder portion 45 generally comprises a rotary solenoid 48, a crank arm 49, a rod 50, a piston 51, cylinder 52, and a pipe 53. The rotary solenoid 48 is adapted to rotate the crank arm 49. The crank arm 49 moves the piston 51 upward through the rod 50 to compress air within the cylinder 52. The compressed air is fed into the chamber 44 through the pipe 53 as a high pressure air. The high pressure air within the chamber 44 is discharged from the fluid discharge nozzle 25 toward the cornea C. The fluid discharge system 46 may comprise a high pressure bomb or spray can and an electromagnetic valve instead of using the piston cylinder 45. Also, it may comprise an air compressor and an electromagnetic valve. The cylindrical body 47 of the chamber 44 is provided with a pressure sensor 54 adapted to measure the air pressure within the chamber 44.

Figure 9:
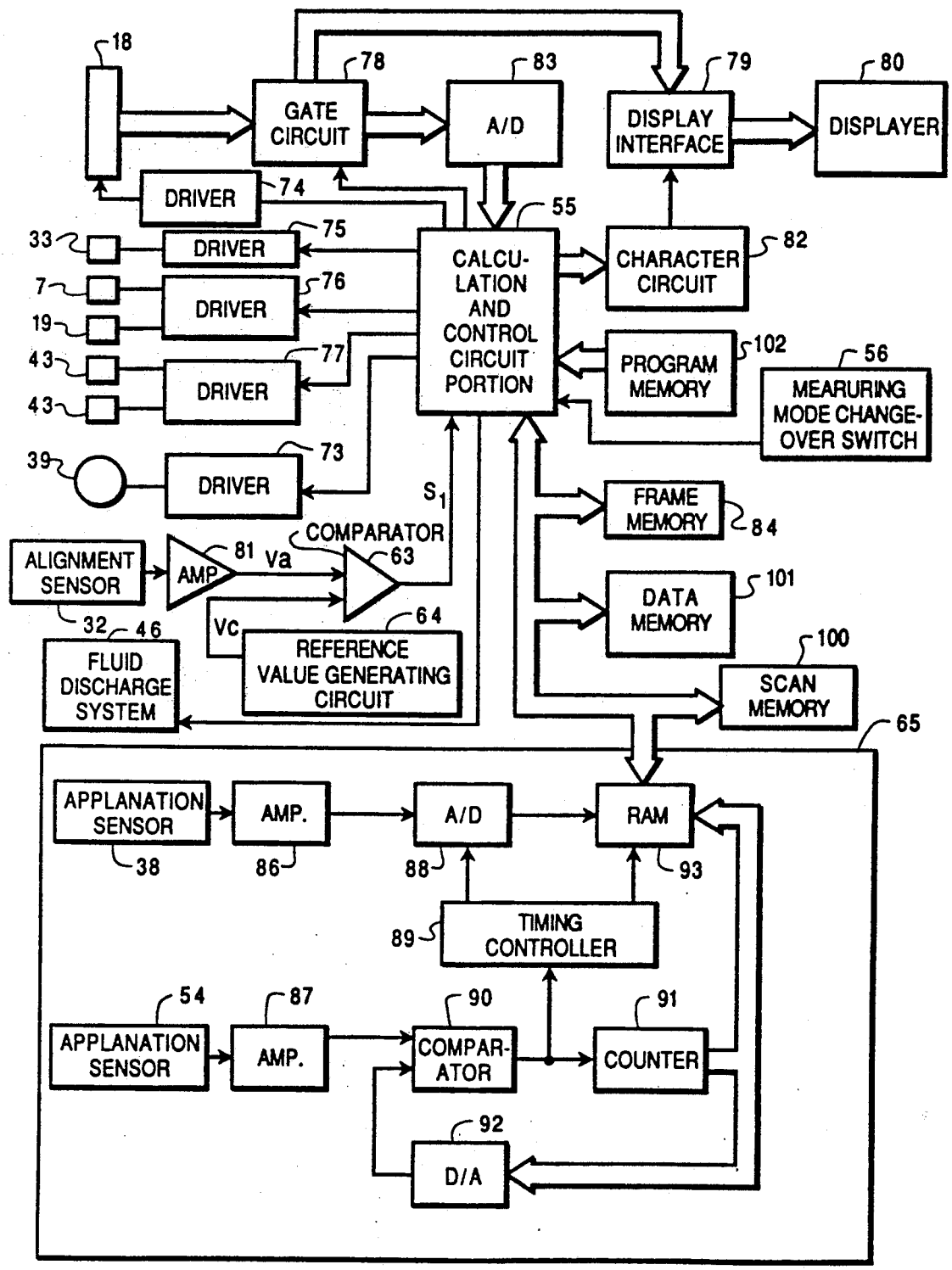
FIG. 9 is a block diagram showing the whole control circuit.

The corneal configuration measuring means and the intraocular pressure measuring means include a control circuit for obtaining the corneal configuration measured value and the intraocular pressure measure value. FIG. 9 shows this control block diagram. In FIG. 9, 55 denotes a calculation and control circuit portion. This calculation and control circuit portion 55 can be switched to a corneal configuration single measuring mode, an intraocular pressure measuring single mode, and both corneal configuration intraocular pressure measuring mode by using a measuring mode changeover switch 56.

Figure 1:
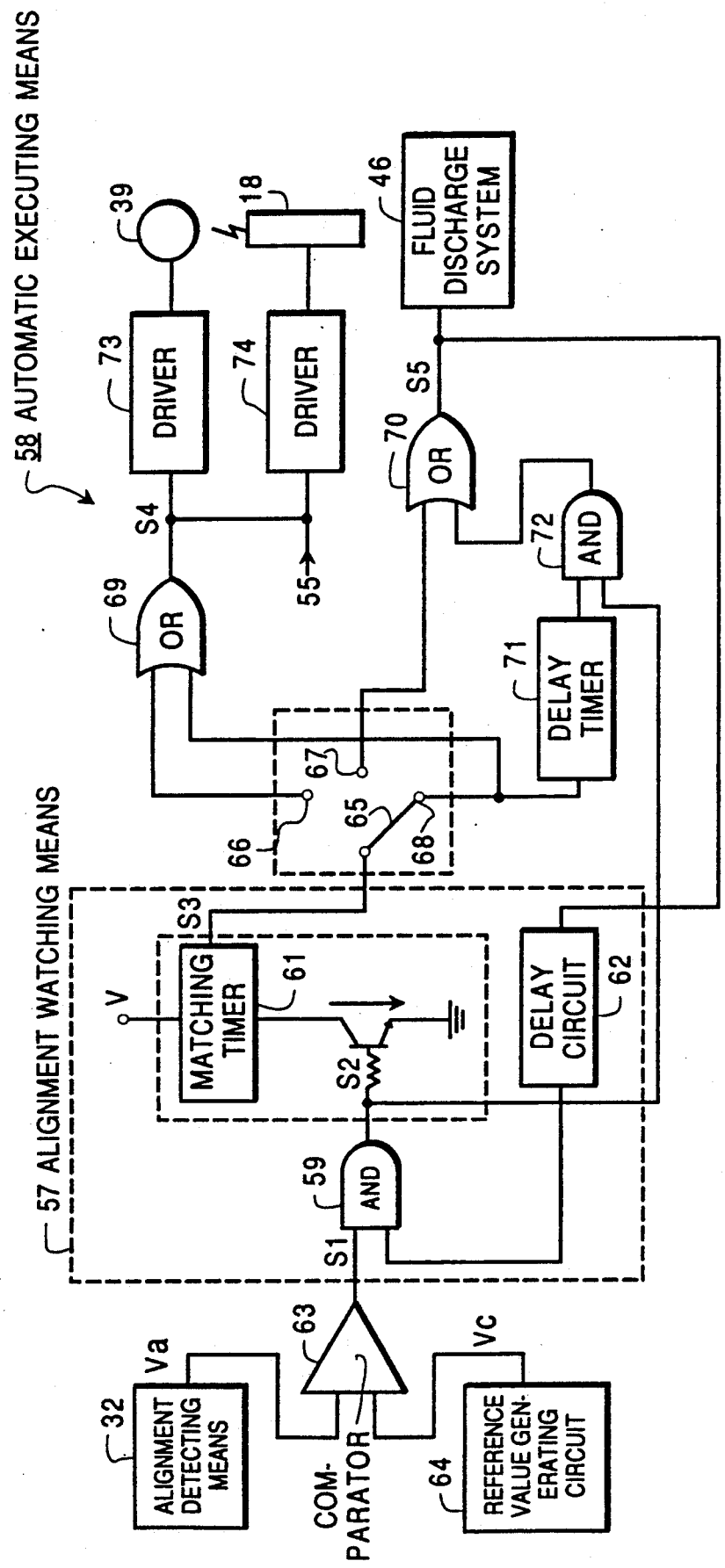
FIG. 1 is a schematic view showing the constitution of an important portion of a control circuit of an ophthalmological instrument according to the present invention.

This arithmetic control circuit portion 55, as shown in FIG. 1, has an alignment watching means 57, and an automatic executing means 58.

The alignment watching means 57 generally comprises an AND circuit 59, a transistor 60, a watching timer 61, and a delay timer 62. An alignment completion signal $S_1$ is input into one input terminal of the AND circuit 59 from a comparator 63. Also, output power of the delay timer 62 is input into the other input terminal of the AND circuit 59.

An output power Va of the alignment sensor 32 is input into one terminal of the comparator 63. A reference output power Vc of the reference value generating circuit 64 is input into the other terminal of the comparator 63. The reference output power Vc is used for judging the alignment completion. The output power Va of the alignment completion signal $S_1$ is "H-level" when the output power Va is larger than the reference output power Vc. The delay timer 62 has such a function as to prohibit that the fluid discharge is started twice continuously within a short period of time. Normally, the output power of the delay timer 62 is "H-level" and when a fluid discharge start signal as will be described is input, the output power becomes "L-level" for a predetermined period of time.

The AND circuit 59 outputs an operating signal $S_2$. The operating signal $S_2$ is input into the transistor 60. The transistor 60 is turned on by the operating signal $S_2$. The watching timer 61 has such a function as that when the transistor 60 is turned on, the watching timer 61 is reset to start the counting. Also, the watching timer 61 has such a function as to output an executing command signal $S_3$ after the counter has been performed for a predetermined period of time.

This executing command signal $S_3$ is input into the automatic executing means 58 through a mode switching contact 65.

The mode switching contact 65 is connected to a terminal 66 when the measuring mode change-over switch 56 is set to the corneal configuration single measuring mode, to a terminal 67 when the switch 56 is set to the intraocular pres-sure single measuring mode and to a terminal 68 when the switch 56 is set to the both corneal configuration intraocular pressure measuring mode. The terminal 66 is connected with one terminal of an OR circuit 69. The terminal 68 is connected with the other terminal of the OR circuit 69 and a delay timer 71.

The delay timer 71 is used to project a ring target mark in order to delay the fluid discharge until the intaking of data regarding the corneal configuration as will be described hereinafter is completed when in the both corneal configuration intraocular pressure measuring mode. The delay timer 71 is connected with one terminal of an AND circuit 72. The other end of the AND circuit 72 is connected with an output terminal of the AND circuit 59. The AND circuit 72 functions as a means for checking whether the alignment is continued when the fluid discharge is started, and the detail thereof will be described hereinafter.

The other end of the OR circuit 70 is connected with an output terminal of the AND circuit 72. This OR circuit 70 is connected with a driver (not shown) for driving the rotary solenoid 48 of the fluid discharge system 46. On the other hand, the OR circuit 69 is connected with drivers 73 and 74. The driver 73 has such a function as to light up the light source 39. The driver 74 has such a function as to scan the area CCD 18. Next, the function of the calculation and control circuit portion 55 will be described together with the operation of the ophthalmological instrument according to the present invention.

The calculation and control circuit 55 lights up the light source 33 through the driver 75 first and then lights up the LED 7 and 19 through the driver 76. Also, it lights up the visible light sources 43, 43 simultaneously through the driver 77. Next, the calculation and control circuit 55 actuates the driver 74 to scan the area CCD 18.

Figure 11:
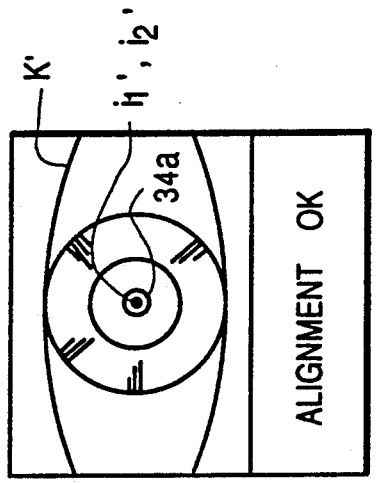
FIGS. 10, 11a, 11b and 12 are illustrations showing display examples of a displayer.
Figure 11:
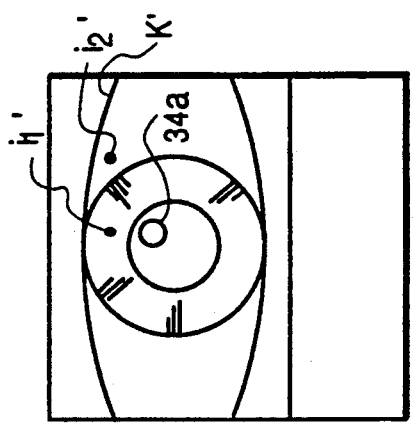

Output power of the area CCD 18 is input the displayer 80 through the gate circuit 78 and the display interface 79. The anterior portion image K', the reticle image 34a, and the alignment target image $i_1'$ and $i_2'$ are displayed on the displayer 80 as shown in FIG. 11a. The measurer moves a mount table (not shown) upward and downward, rightward and leftward, and forward and backward while looking a displaying screen (FIG. 11a) and moves the apparatus body as such that the alignment target images $i_1'$ and $i_2'$ are brought to be coincident with each other at the center of the reticle image 34a as shown in FIG. 11b. By this, the alignment axial line On is brought to be coincident with the vertex P of the cornea C and obtains a predetermined working distance 1 (see FIG. 7).

The output power Va of the alignment sensor 32 is amplified by an amplifier 81 (omitted from FIG. 1) and then compared with the reference output power Vc from the reference value generating circuit 64 by the comparator 63. When the alignment verification is completed, the comparator 63 outputs the alignment completion signal $S_1$ to the watching means 57 as described. At the same time, the calculation and control circuit 55 actuates the character circuit 82 and displays "alignment OK" on the displayer 80 through the display interface 79.

Now suppose that the measuring mode change-over switch 56 is set to the corneal configuration single measuring mode.

Figure 12:
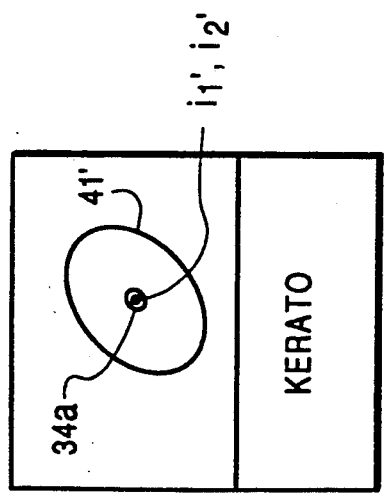

When the measuring mode change-over switch 56 is set to the corneal configuration single measuring mode, the calculation and control circuit 55 turns off the drive signal to the driver 77 and puts off the visible light sources 43, 43 upon receipt of the alignment completion signal $S_1$. Also, the calculation and control circuit portion 55 switches over the gate circuit 78 and sets as such that the output power of the area CCD 18 is input into the A/D converter 83. At the same time, the calculation and control circuit portion 55 controls as such that the character circuit 82 displays "KERATO" meaning corneal configuration measurement on the displayer 80 through the character circuit 82 (see FIG. 12). On the other hand, the alignment watching means 57 outputs the operating signal $S_2$ when the AND circuit 59 receives the alignment completion signal $S_1$.

When the transistor 60 is turned on in accordance with the operating signal $S_2$, the watching timer 61 is reset to clear the counted content and starts counting newly. The counting period of time is about 0.2 seconds taking into consideration the tremor of the sight fixation of the eye. In some cases, even when the alignment verification is not completed yet, the alignment completion signal $S_1$ is accidentally output as shown by reference character $S_1'$ of FIG. 2 and the watching timer 61 starts counting due to the tremor of the sight fixation of the eye. However, as the period of time for the alignment completion signal $S_1$ to be in "H-level" is by far shorter than 0.2 seconds, the watching timer 61 stops counting as soon as the transistor 60 stops operation and no executing command signal $S_3$ is output.

Now suppose that the apparatus body has been properly aligned with the eye. In this embodiment, when the alignment completion state is continued for more than 0.2 seconds, that is, when the period of time for the output power of the alignment completion signal $S_1$ to be in "H-level" is maintained for more than 0.2 seconds as shown by the reference character $S_0$ of FIG. 2, the watching timer 61 finishes the counting for the predetermined period of time and outputs the executing command signal S3. This executing command signal S3 is input into the drivers 73 and 74 as a ring target mark projection starting signal S4 through the OR circuit 69. By this, the light source 39 is lighted up and the scanning of the area CCD 18 is started.

In this embodiment, the anterior portion of the eye is not illuminated by the visible light sources 43, 43. As a consequence, the anterior portion image is not formed on the CCD 18. Instead, the light source 39 is lighted up and the ring-shaped pattern 41 is projected onto the cornea C of the eye and the corneal reflected pattern image 41' of the ring-shaped pattern 41 is formed on the CCD 18 by the objective lens 26 and the imaging lens 29. As a result, the corneal reflected pattern image 41' is displayed on the displayer 80 (see FIG. 12).

At this time, the output power of the area CCD 18 is input into the A/D converter 63 through the gate circuit 78. The A/D converted digital signal is input into the frame memory 84 through the calculation and control circuit 55. The frame memory 84 memorizes one frame portion of information of the CCD 18. In this way, the data regarding the corneal configuration is intaken and the calculation as will be described is carried out.

The calculation of the corneal configuration is carried out in the manner as will be described hereunder.

Figure 14:
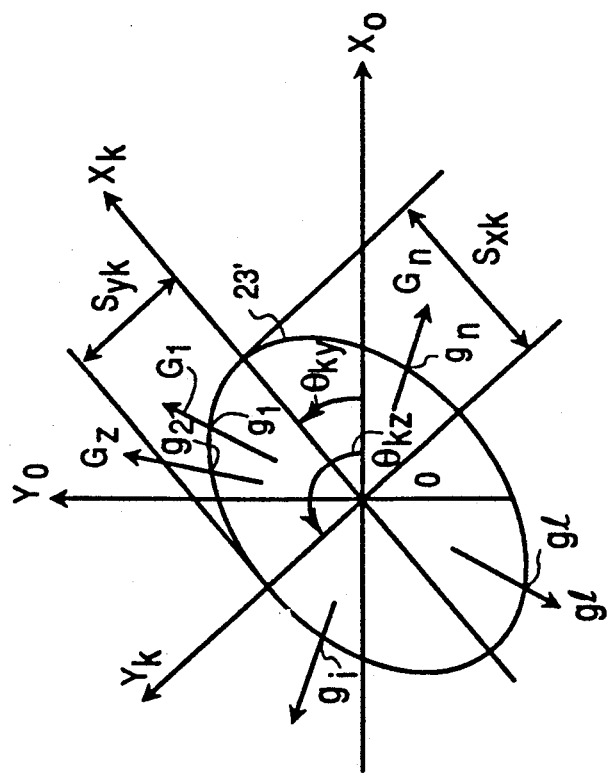
FIG. 14 is an illustration showing a relation between a cornea reflected pattern image and a read scanning line.
Figure 16:
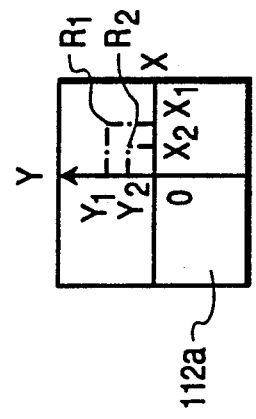
FIGS. 16 through 20 are explanatory views of the embodiments in which a position sensor is used as the alignment sensor.

The calculation and control circuit 55 reads the image data of the corneal reflected pattern image 41' stored in the frame memory 84 in accordance with memory reading scanning lines $G_1, G_2, \ldots, G_1 \ldots, G_1, \ldots, G_n$ which are stored in the scan memory 100 beforehand. The memory reading scanning lines $G_1, G_2, \ldots, G_1 \ldots, G_1, \ldots, G_n$ scan the data of the frame memory 84 radially about the origin O of the $X_0$-$Y_0$ coordinate as shown in FIG. 14.

And the coordinate of points $g_1, g_2, \ldots, g_1, \ldots, g_1, \ldots, g_n$ on the corneal reflection pattern image 41' is obtained.

The calculation and control circuit 55 calculates the elliptical configuration of the pattern image 41' from such obtained coordinate $g_1, g_2, \ldots, g_1, \ldots, g_1, \ldots, g_n$.

The radius $S_{xk}$ of the long axis (XK axis) of the ellipse corresponds to the radius of curvature $R_1$ of the weak primary meridian of the cornea C. The radius $S_{yk}$ of the short axis (Yk axis) corresponds to the radius of curvature $R_2$ of the strong primary meridian.

The angle $\theta_{k1}$ of the long axis and the angle $\theta_{k2}$ of the short axis correspond to the axial angle $\theta_1$ of the strong primary meridian and the axial angle $\theta_2$ of the weak primary meridian, respectively.

A general relation of the ellipse in the x-y coordinate is expressed as follows;

$$Ax^2 + By^2 + Cxy = 1 \quad (1)$$

$$A = \frac{\cos^2\theta_{k1}}{(2S_{xk})^2} + \frac{\sin^2\theta_{k1}}{(2S_{yk})^2}$$

$$B = \frac{\sin^2\theta_{k1}}{(2S_{xk})^2} + \frac{\cos^2\theta_{k1}}{(2S_{yk})^2} \quad (2)$$

$$C = \frac{2\sin\theta_{k1} \cdot \cos\theta_{k1}}{(2S_{xk})^2} + \frac{2\sin\theta_{k1} \cdot \cos\theta_{k1}}{(2S_{yk})^2}$$

Also, given that the radius $S_k$ of the corneal reflected pattern image 41' is r, the radius of the ring-shaped pattern 23 is h, the working distance is, and the whole power of the ring target image projecting optical system 4 and the anterior portion observing system 2 is $\beta$, the radius $S_k$ of the ring-shaped pattern image 41' has the following relation.

$$S_k = Y \times \beta$$

$$Y = h \times r/2\ l$$

Therefore, $S_{xk}$ and $S_{yk}$ are found from the relations (1) and (2), and the radius of curvature $r_1$ of the strong primary meridian can be obtained from the following relation;

$$r_1 = \frac{2S_{xk} \cdot l}{\beta \cdot h} \quad (4)$$

Similarly, the radius of curvature $r_1$ of the strong primary meridian can be obtained from the following relation;

$$r_2 = \frac{2S_{xk} \cdot l}{\beta \cdot h} \quad (4')$$

Also, the axial angle $\theta_1$ of the strong primary meridian can be obtained as $\theta_1 = \theta_{k2}$ and the axial angle $\theta_2$ of the weak primary meridian can be obtained as $\theta_2 = \theta_{k1}$. Such obtained radii of curvature $r_1$ and $r_2$ and axial angles $\theta_1$ and $\theta_2$ are stored in the data memory 101.

Next, the measuring mode change-over switch 56 is set to the intraocular measuring mode.

Figure 10:
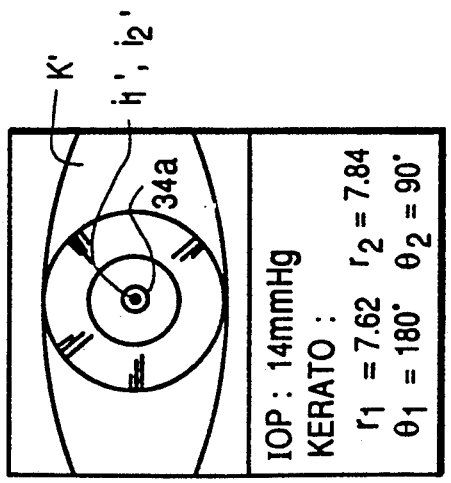

After the data regarding the corneal configuration is intaken, the measuring mode change-over switch 56 is switched from the corneal configuration single measuring mode to the intraocular pressure single measuring mode in succession. Consequently, the calculation and control circuit portion 55 puts off the visible light source 39 to stop the projection of the ring-shaped pattern 41. At the same time, the calculation and control circuit 55 lights up the light sources 43, 43 again to illuminate the anterior portion. Also, the calculation and control circuit 55 switches over the gate circuit 78. By this, the output power of the area CCD 83 is switched over from the A/D converter 78 to a display interface 79. As a consequence, as shown in FIG. 10, the anterior portion image k', the reticle image 34a, the alignment target images $i_1'$, $i_2'$ are displayed again on the displayer 80.

The signal processing system 85 of the intraocular pressure measuring means will now be described before the operation of the intraocular pressure is described in detail.

The signal processing system 85 includes an amplifiers 88, 87, an A/D converter 88, a timing controller 89, a comparator 90, and counter 91. The A/D converter 88 has such a function as to convert the applanation signal (corneal reflected light quantity signal) of the applanation sensor 38 which is input through the amplifier 86 into a digital signal and runs the A/D conversion in accordance with the signal command of the timing controller 89.

The comparator 90 compares the pressure signal of the pressure sensor 54 which is input therein through the amplifier 87 with the count analog signal obtained by converting the counted number of the counter 91 by the D/A converter 92. The output power of the comparator 90 is H-level when the pressure signal value is more than the count analog value and L-level when less than the count analog value. The timing controller 89 outputs a command signal for actuating the A/D converter 88 when the output power of the comparator 90 is H-level, and memorizes the digital signal, which has been converted by this A/D converter 88, in the RAM 93. When the output power of the comparator 90 is changed from L-level to H-level, the counter 91 increases the count number by 1 and designates the addresses of the RAM 93 in succession. The RAM 93 memorizes the A/D converted digital signal converted by the A/D converter 88 in the designated address.

Presuming that the count content of the counter 91 is zero in this embodiment, first, when the electric potential of the pressure signal is raised, the output power of the comparator 90 becomes H-level.

As a consequence, the counted content of the counter 91 becomes "1". The D/A converter 92 D/A converts the signal corresponding to the counted content "1" of the counter 91 and outputs the same to the comparator 90 as a count analog signal. At the next time point, the comparator 90 compares the count analog signal with the pressure signal.

At this time, as the rising of the electric potential of the pressure signal corresponding to the rising of the pressure of the air pulse from the time point when the output power of the comparator 90 is changed to H-level till the output power of the D/A converter 92 becomes less than the electric potential of one bit portion of the D/A converter 90.

Accordingly, the output power of the comparator 90 becomes L-level again. By a loop comprising such comparator 90, counter 91, and the D/A converter 92, as the count number of the counter 91 is increased in accordance with the pressure increase of the air pulse. Therefore, the count number corresponding to the pressure of the air pulse is memorized. Also, as the count number sequentially designates the addresses of the ram 93, the address and the pressure of the air pulse are corresponded with each other.

When the alignment verification is completed and the alignment completion state is continued for a predetermined period of time, the watching timer 61 outputs an executing command signal $S_4$ toward the OR circuit 70. As a consequence, the OR circuit 70 outputs the fluid discharge starting signal $S_5$, the fluid discharge system 46 is actuated, and discharges the air pulse from the fluid discharge nozzle 25 to the cornea C. On the other hand, the pressure sensor 38 outputs the pressure signal corresponding to the air puff to the A/D converter 88. The comparator 90 compares this pressure signal with the count analog signal which is output from the D/A converter 92.

In this case, as the count number of the counter 91 is reset to zero, the pressure signal value becomes more than the count analog signal. By this, the output power of the comparator 90 is brought to H-level for L-level and the count number of the counter 91 becomes "1". The signal of this count number "1" is converted to a count analog signal by the D/A converter 92 and compared with the pressure signal. At this time, as the output power of the D/A converter 92 is set to be larger than the pressure increase of the air pulse when the count is increased by "1", the count analog signal becomes larger than the pressure signal, and the pressure signal of the comparator 90 is brought to L-level from H-level again. And the pressure of the air puff is increased as time passes and the count number is increased by "1" every time the pressure signal becomes larger than the analog signal.

And when the cornea C, as shown in FIG. 6, is made applanation in accordance with the increase of the pressure of the air pulse, the applanation signal output from the applanation sensor 38 becomes maximum.

Thereafter, as the pressure increases, the corneal is brought to a concave shape. As a consequence, the signal value of the applanation signal is reduced.

On the other hand, the timing controller 89 outputs a command signal every time the output power of the comparator 90 becomes H-level.

Figure 13:
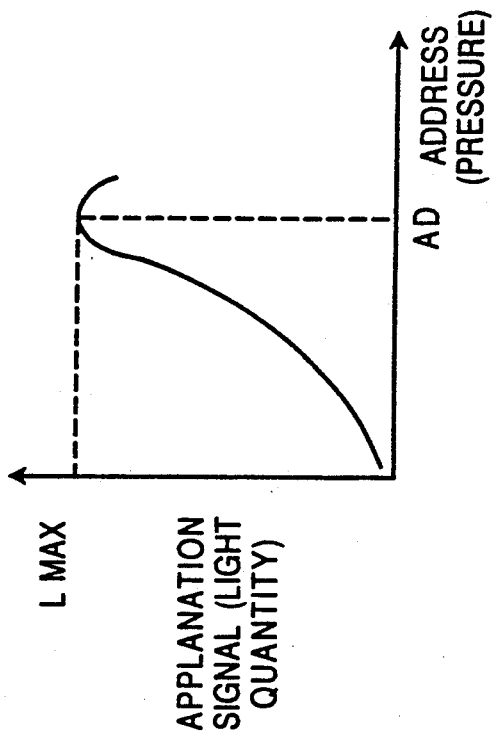
FIG. 13 is an illustration showing a relation between the address of RAM 93 and an applanation signal.

The A/D converter 88 converts the applanation signal, which is output from the applanation sensor 38, to an applanation digital signal every time it receives the command signal. And the RAM 93 memorizes the applanation digital signal in the address designated by the counter 91 as shown in FIG. 13. As this address corresponds to the pressure of the air pulse, the address (AD), which memorizes the maximum value of the applanation digital signal is correlated with the intraocular pressure of the eye. In this way, data for obtaining the intraocular pressure value is obtained.

The calculation and control circuit 55 reads the corneal reflection light quantity data which are stored in the RAM 93 and compares the various data. And the calculation and control circuit 55 finds the address AD where the maximum light quantity Lmax (see FIG. 13) is stored and calculates the intraocular pressure IOP from the following predetermined intraocular pressure converting formula;

$$IOP = a(AD) + b \qquad (5)$$

in accordance with the address value AD, and such obtained IOP value is stored in the data memory 101.

Figure 2:
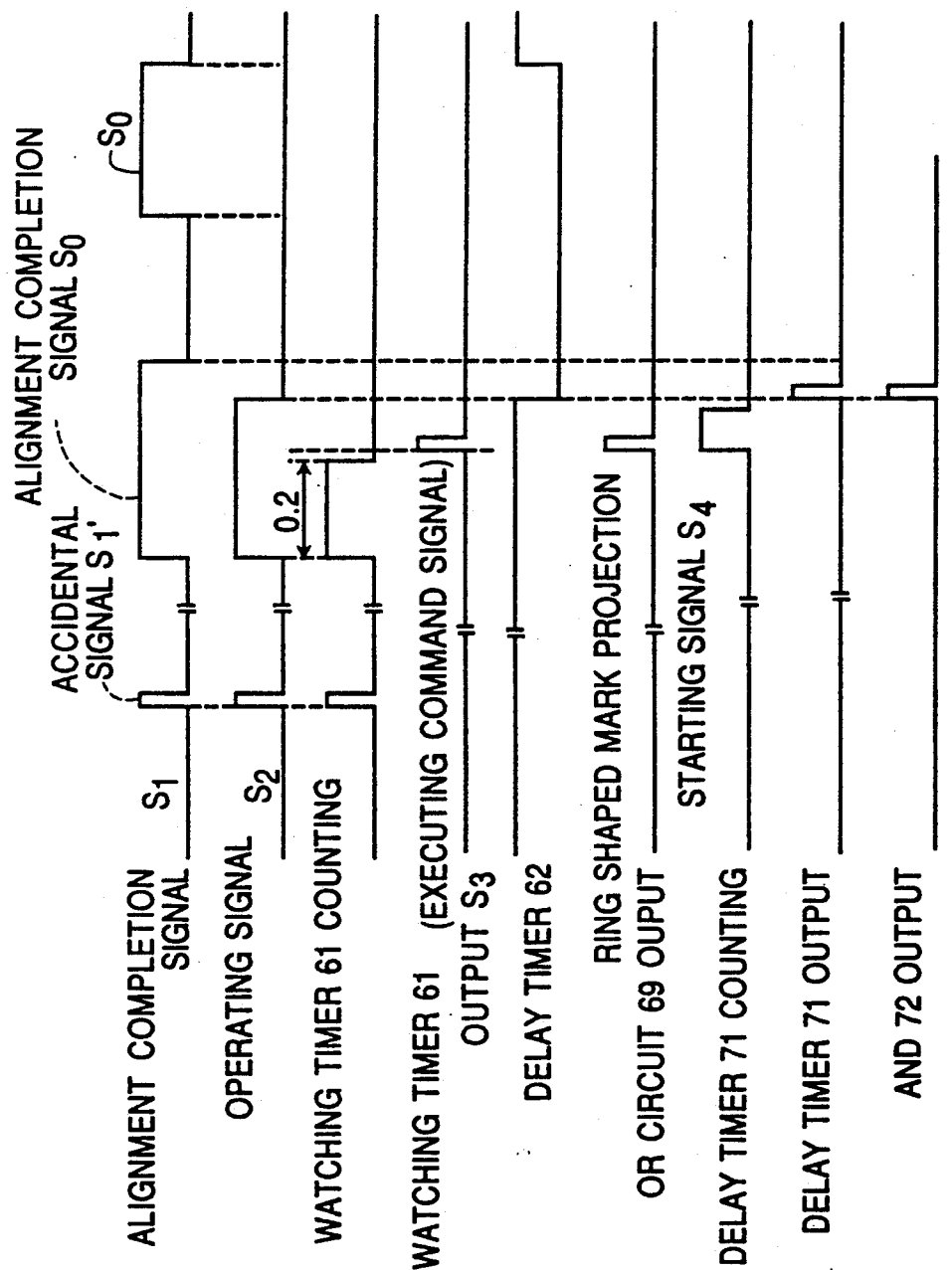
FIG. 2 is a timing chart of the measuring mode for both corneal configuration and intraocular pressure of the control circuit.

Next, suppose that the output power of the OR circuit 70 is H-level, the output power of the delay timer is brought to H-level from L-level as shown in FIG. 2 and the output power of the delay timer 62 is brought to L-level for a predetermined period of time, Since the output power of the OR circuit 70 is input into the delay timer 62. In this embodiment, the period of time for the output power of the delay timer 62 being stayed in L-level is established taking into consideration, for example, the period of time for the air being intaken into the cylinder of the fluid discharge system 46.

Accordingly, when the output power of this delay timer 62 becomes L-level, the operating signal of the AND signal 59 is brought to L-level from H-level, and the watching timer 61 stops counting. Thereafter, even if the alignment completion state should be continued, the watching timer 61 does not output the executing command signal $S_3$, and thus it is prohibited that the fluid discharge is carried out twice in succession. For example, even if the fluid discharge is carried out in accordance with the preceding alignment completion and then the alignment completion is detected in succession, the watching timer 61 does not output the executing command signal $S_3$.

Next, there will be described a case where the measuring mode change-over switch 56 is changed over to the both corneal configuration measuring.intraocular pressure measuring mode in order to carry out the corneal configuration measurement and the intraocular pressure measurement successively.

When the measuring mode change-over switch 56 is set to the both corneal configuration measuring.intraocular pressure measuring mode, the contact point 65 is brought into contact with the terminal 68. The calculation and control circuit portion 55 lights up the light source 33, the LEDs 7 and 19, and the visible light sources 43, 43 as in the single measuring mode by means of operation of the measuring mode changeover switch 56. And when the alignment operation is performed, the alignment completion signal $S_1$ is output as in the case with the single measuring mode.

When the alignment completion state is continued for a predetermined period of time, the watching timer 61 judges as "alignment OK" (see Step $S_1$ of FIG. 3) and outputs the executing command signal $S_3$ to the OR circuit 59 and the delay timer 71. After intaking the data regarding the corneal configuration, the delay timer 71 starts discharging the air pulse and starts counting in accordance with the executing command signal $S_3$ as shown in FIG. 2. On the other hand, the OR circuit 69 outputs the ring-shaped target mark projection starting signal $S_4$ to the drivers 73 and 74 upon input of the executing command signal $S_3$. By this, the drivers 73 and 74 are driven as already described in the corneal configuration single measuring mode and the data regarding the corneal configuration is memorized in the frame memory 84 (see Step $S_2$ of FIG. 3).

When the delay timer 71 finishes the counting of a predetermined time, it outputs pulse to the AND circuit 72 as shown in FIG. 2. When the operating signal $S_2$ of the AND circuit 59 is H-level, that is, when the alignment completion state is continued even after the data regarding the corneal configuration is intaken, the AND circuit 72 outputs pulse toward the OR circuit 70. When the the alignment completion state is not established immediately after the data regarding the corneal configuration is intaken, the AND circuit 72 does not output pulse.

Therefore, the AND circuit 72 checks whether the alignment completion state is still continued even after the data regarding the corneal configuration (see Step $S_3$ of FIG. 3), and when the alignment completion state is still continued, the OR circuit 70 outputs the fluid discharge start signal $S_5$ toward the fluid discharge system 46. As a consequence, the pulse discharge is started and the data regarding the intraocular pressure of the eye is intaken into the data memory 101 as described in the intraocular single measuring mode (see Step $S_4$ of FIG. 3).

Figure 3:
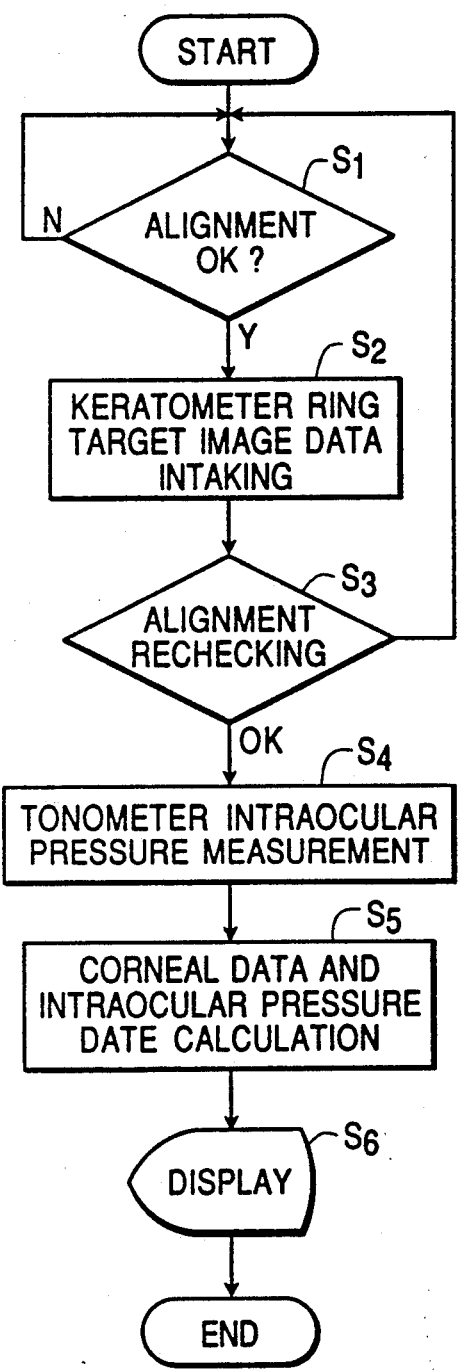
FIG. 3 is a flow chart of the measuring mode for both the corneal configuration and intraocular pressure.

And the calculation and control circuit portion 55 calculates the corneal configuration measuring data and the intraocular pressure measuring data (see Step $S_6$) of FIG. 3 and displays the measured data $r_1$, $r_2$, $\theta_1$, $\theta_2$ and IOP, which are memorized in the data memory 101, on the displayer 80 in digital mode, as shown in FIG. 10, through the character circuit 82 and the display interface 79 (see Step $S_6$ of FIG. 3).

The various actions of the corneal configuration single measuring mode, the intraocular pressure single measuring mode, and the both corneal configuration and intraocular measuring mode are carried out in accordance with the sequence program which is memorized in the program memory 102.

Figure 15:
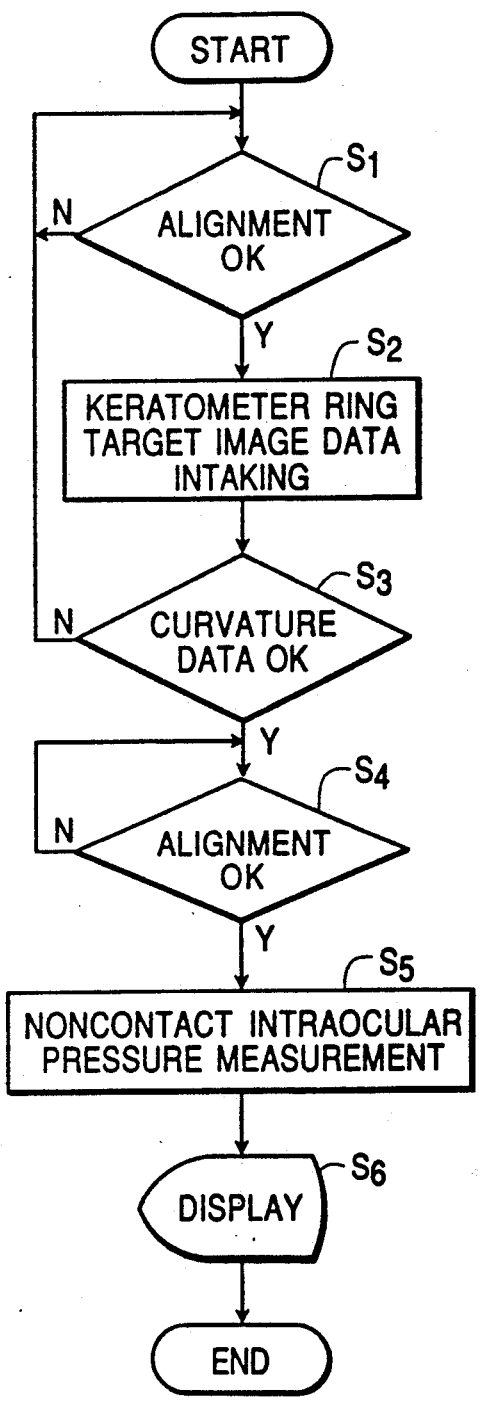
FIG. 15 is a flow chart for explaining another embodiment of the measuring mode for both the corneal configuration and anterior pressure.

FIG. 15 shows another embodiment of the calculation and control circuit portion 55 when the corneal configuration measurement and the intraocular pressure measurement are carried out in succession. The calculation and control circuit portion 55 causes the frame memory 84 to memorize the data of the ring target image after confirming the "alignment OK" (Step $S_2$). And the calculation and control circuit portion 55 calculates the radii of curvature $r_1$ and $r_2$. And the calculation and control circuit portion 55 confirms whether the data of the radii of curvature $r_1$ and $r_2$ is obtained (Step $S_3$).

Under the condition that the data regarding the radii of curvature $r_1$ and $r_2$ of the cornea and the alignment are continuously proper (see Step $S_4$), that is, when the calculation and control circuit portion 55 has checked that the radii of curvature $r_1$ and $r_2$ of the cornea C are obtained and the alignment completion state is continued after the corneal configuration is measured, it goes to the intraocular measurement (Step $S_5$). Accordingly, the calculation and control circuit portion 55 functions as a data check means for checking whether the data regarding the radius of curvature of the cornea is obtained.

FIGS. 16 through 20 are illustrations for explaining the embodiment in which a position sensor 112 is used as the alignment sensor 32.

The position sensor 112 is adapted to output an electric current corresponding to the positions of the imaging points $R_1$ and $R_2$ on a light receiving surface 112a, that is, an electric current carrying X and Y information in X and Y plane (see FIG. 16) as the light receiving surface 112a from four output terminals 112b through 112e, and the imaging point position on the light receiving surface 112a is found from the electric current values which are output from these four output terminals 112b through 112e.

Figure 17:
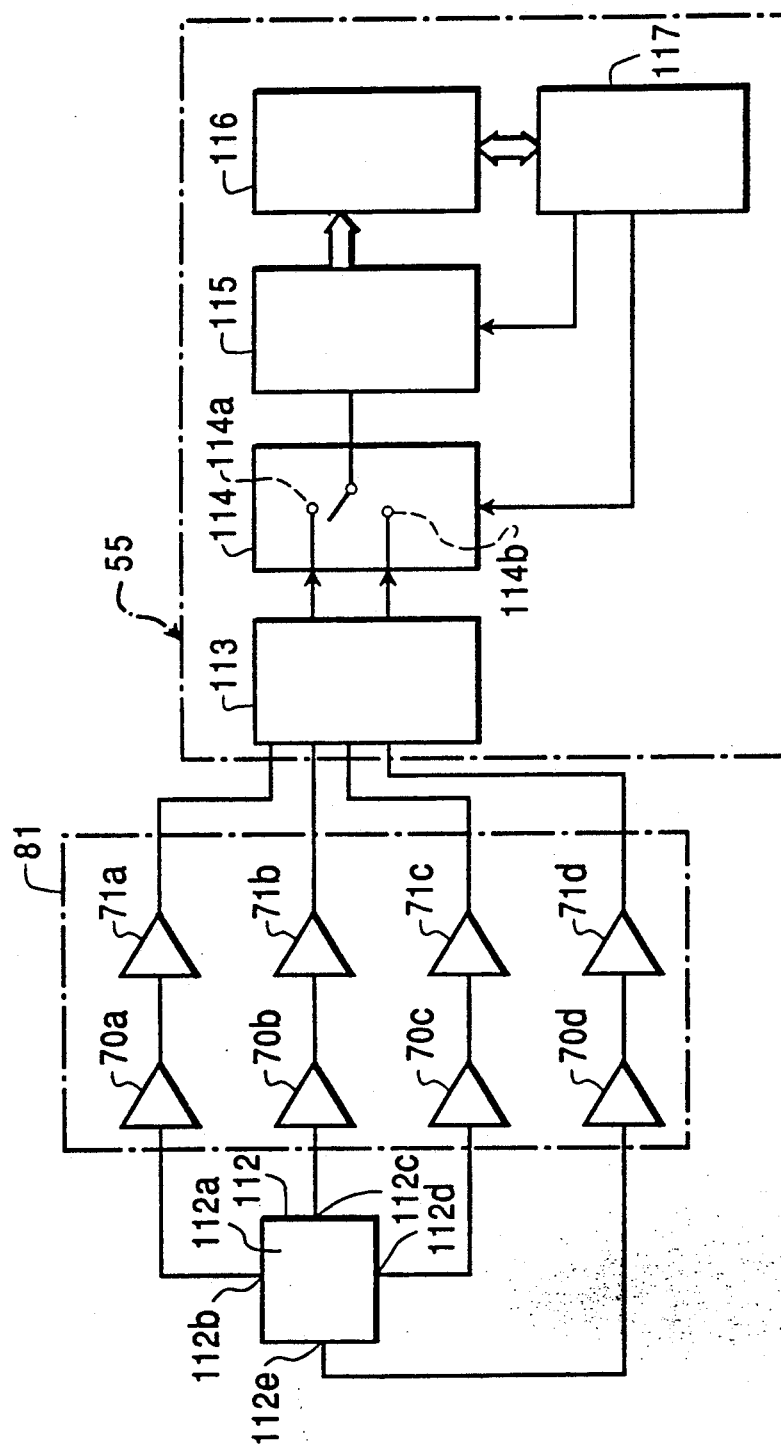
Figure 18:
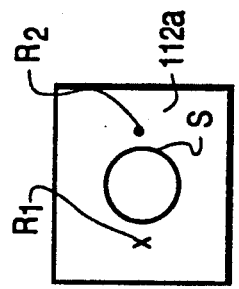
Figure 18:
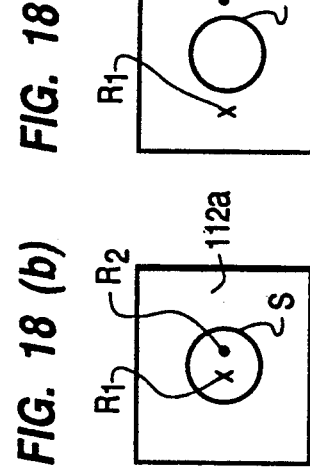
Figure 18:
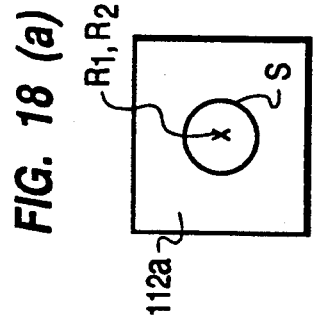
Figure 18:
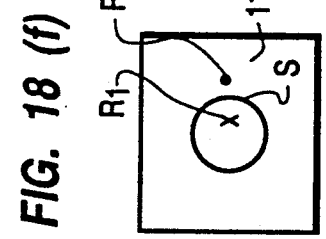
Figure 18:
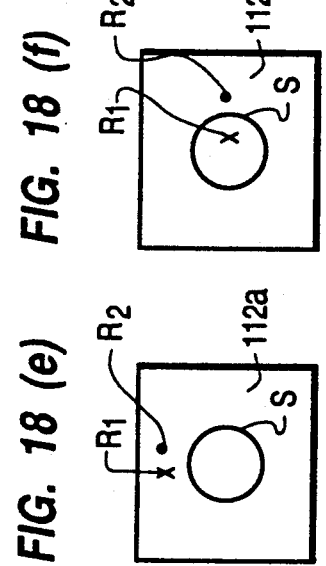
Figure 18:
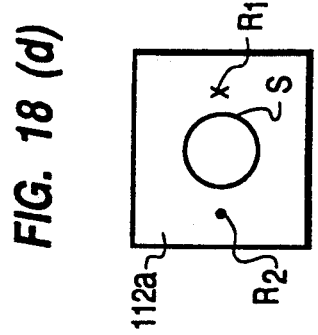

In this embodiment, FIG. 17 is a detailed block diagram of an alignment detecting means. In this embodiment, there are not provided the comparator 63, the reference value generating circuit 64, the alignment watching means 57, and the automatic executing means 58 which are shown in FIG. 1. The diaphragm 31 of FIG. 4 is not shown, either. That is, the position sensor 112 is connected to the calculation and control circuit portion 55 through the amplifier 81.

In FIG. 17, the reference numerals 70a through 70d denote I/V converting circuits for converting the electric current, which is output from the various output terminals 112b through 112e of the position sensor 112, to an electric voltage corresponding to the value, 71a through 71d denote amplifiers, and 113 denotes an analog calculation circuit for calculating the (X, Y) coordinate position of the imaging point R on the light receiving surface 112a of the position sensor 112 with reference to the electric voltages which are output from the various amplifiers 71a through 71d.

The numeral 114 denotes an analog switch circuit. When the analog calculation circuit 113 is calculating the X coordinate, the analog switch circuit 114 closes the contact 114a and outputs an electric voltage corresponding to each calculated X coordinate value. On the other hand, when the analog calculation circuit 113 is calculating the Y coordinate, the analog switch circuit 114 closes the contact 114b and outputs an electric value corresponding to the calculated Y coordinate value. The numeral 115 denotes an A/D converter for converting the electric voltage of the X and Y coordinate value, which is output from the analog switch circuit 114 to a digital signal. The numeral 116 denotes a memory circuit adapted to memorize the X and Y coordinate value as a digital signal which is output from the A/D converter 115.

The numeral 117 denotes a control portion for controlling the blinking of the LEDs 7 and 19, the switching action of the analog switch circuit 114, the converting timing of the A/D converter 115, and the like. Also, this control portion 117 judges whether the points $R_1$ and $R_2$ of the X and Y coordinate memorized in the memory circuit 116 is within a preset range S on the light receiving surface 112 as shown in FIGS. 18(a) through 18(f) and, if within the preset range S, detects the alignment completion state.

As is shown in FIGS. 18(a) through 18(f), an image due to the virtual image $i_1$ is imaged at the point $R_1$ of the light receiving surface 112a of the position sensor 112. Then, an electric current corresponding to the point $R_1$ is output from the output terminals 112b through 112e of the position sensor 112. The coordinate $X_1$ and $Y_1$ at the point $R_1$ is calculated by the analog calculation circuit 113 from these electric current values. The coordinate $X_1$ and $Y_1$ at the point $R_1$ is memorized in the memory circuit 116 through the analog switch 116 and the A/D converter 115.

After memorization, the LED 19 is lighted up by the control portion 117, the LED 7 is turned off, and the target image is formed on the eye E as a virtual image $i_2$ in the same manner as described above. And the image due to the virtual image $i_2$ is formed at the point $R_2$ of the light receiving surface 112a of the position sensor 112 by the first optical system 5. Then, electric current corresponding to the point $R_2$ is output from the output terminals 112b through 112e of the position sensor 112. The coordinate $X_2$ and $Y_2$ at the point $R_2$ is calculated from these electric current values by the analog calculation circuit 113.

The control portion 117 judges whether the the imaging points $R_1$ and $R_2$, which are memorized by the memory circuit 116, are within the preset range S. The present range S and the reticle image 34a are set to a corresponding size.

And when the axial line On of the fluid discharge nozzle 25 and the alignment axial line of the eye are in alignment with each other and the distance between the eye E and the fluid discharge nozzle 25 is a predetermined length, the imaging points $R_1$ and $R_2$ are overlapped at the center of the present range S as shown in FIG. 18(a). In that state, the control portion 117 outputs an alignment completion signal.

Also, in the case of FIG. 18(b), the axial line On of the fluid discharge nozzle 25 and the alignment axial line of the eye are generally in alignment with each other, and the distance between the eye and the fluid discharge nozzle 25 is a generally predetermined length. Accordingly, the control portion 117 outputs an alignment completion signal. In this way, as the control portion 117 outputs the alignment completion signal after judging whether the imaging points $R_1$ and $R_2$ are within the preset range S, the alignment state of the ophthalmological instrument with respect to the eye E can be detected accurately irrespective of influence of the reflective index of the eye E, light coming from outside or the like.

Also, the alignment operation for bringing the target within the preset range S can be performed easier than the operation for making the imaging points $R_1$ and $R_2$ to be completely coincident with each other as shown in FIG. 18(a).

In the example shown in FIG. 18(c), the axial line On of the fluid discharge nozzle 25 and the axial line of the alignment of the eye are generally coincident with each other, and the distance between the eye and the fluid discharge nozzle 25 is shorter than the predetermined length. In the example shown in FIG. 18(d), the axial line On of the fluid discharge nozzle 25 and the axial line of the alignment of the eye are generally in coincident with each other, and the distance between the eye and the fluid discharge nozzle 25 is longer than the predetermined length.

In the example shown in FIG. 18(e), the distance between the eye and the fluid discharge nozzle 25 is the generally predetermined length, and the axial line On of the fluid discharge nozzle 25 is displaced in the vertical direction from the axial line of the alignment axial line of the eye. In the example shown in FIG. 18(f), the distance between the eye and the fluid discharge nozzle 25 is the generally predetermined length, and the axial line On of the fluid discharge nozzle 25 is displaced in the horizontal direction from the alignment axial line of the eye.

In the above-mentioned embodiments, the positions of the imaging points $R_1$ and $R_2$ of the target mark are detected using the position sensor 112. However, it may be designed such that the positions of the imaging points $R_1$ and $R_2$ are detected using, for example, an area CCD as an area image sensor. In this case, if the target marks are designed in such a manner as to be mutually distinguishable, the LEDs 7 and 19 are no more required to be blinked alternately.

Upon completion of the alignment verification, the calculation and control circuit portion 55 actuates the character circuit 82 and displays "alignment OK" on the displayer 80 through the display interface 79.

In this embodiment, the alignment verification is to bring the alignment target images $i_1'$ and $i_2'$ within the reticle image 34a and not to bring them completely coincided with each other. As a consequence, the value Z of the working distance is sometimes different from the actual value. As a tolerance or allowable range is broad in the intraocular measurement, a generally proper measurement can be performed.

However, errors in the working distance greatly affects the measured value in the corneal configuration measurement. Therefore, if the corneal configuration is measured through the above-mentioned calculation, a proper value cannot be obtained. Therefore, after the measured value is corrected with reference to the error amount in the working distance, the corneal configuration is calculated.

The error amount $\Delta Z$ in the working distance is obtained as follows.

Figure 20:
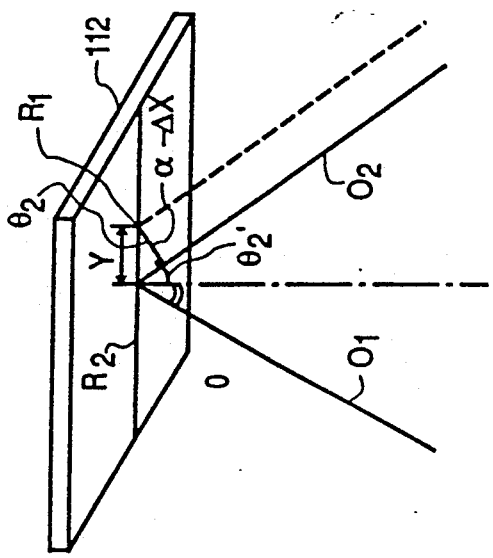
Figure 19:
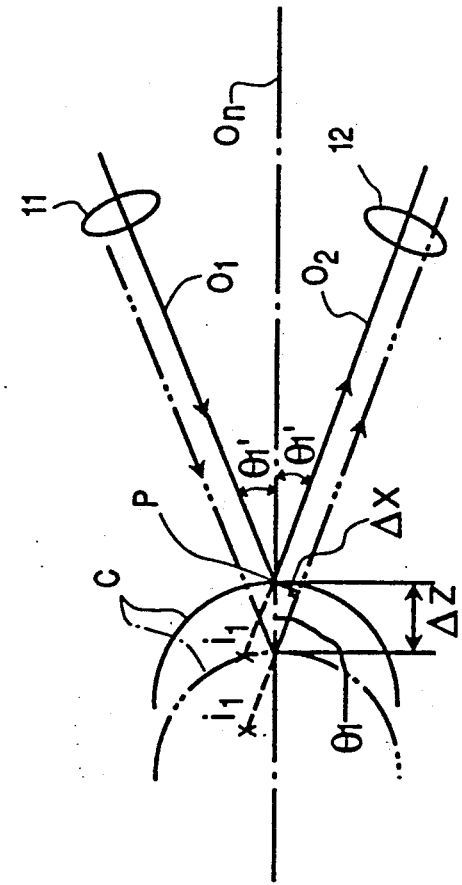

When the axial line On of the fluid discharge nozzle 25 and the alignment axial line of the eye are brought into alignment with each other and the working distance is not correctly coincident with each other, for example, when they are displaced as shown by the two dotted chain lines in FIG. 19 for example, given that the displaced amount (error amount of the working distance) is represented by $\Delta Z$, the imaged point $R_1$ comes to a position on the position sensor 112 away from the center O by a distance y as shown in FIG. 20.

The relation between the working distance error amount $\Delta Z$ and the distance y can be obtained from FIG. 19 as follows;

$$\Delta Z \cdot \sin \theta_1' = \Delta x$$

wherein $\theta_1'$ is an angle between the axial line On of the fluid discharge nozzle 25 and the optical axis $O_2$ of the second optical system 6 and $\Delta x$ is a displaced amount between the optical axis $O_2$ of the second optical system 6 and the ray.

Also, there can be obtained the following relation from FIG. 20;

$$y \cdot \cos \theta_2' = a \cdot \Delta x$$

wherein $\theta_2'$ is an angle between optical axis $O_2$ of the second optical system 6 and axis line perpendicular to center O of position cencer 112. $a$ is the magnification or power of the second optical system 6.

Accordingly, there can be obtained the following relation from the above-mentioned two relations;

$$y \cdot \cos\theta_2' = a \cdot \Delta z \cdot \sin\theta_1'$$

$$\Delta Z = \frac{y \cdot \cos\theta_2'}{a \cdot \sin\theta_1'}$$

From the above relation, the working distance error amount $\Delta Z$ is calculated and the actual working distance becomes $(Z + \Delta Z)$. By calculating the above-mentioned formula, etc. based on this, there can be measured a proper corneal configuration which is not affected by the error of the working distance.

Also, it can be obtained as strong primary meridian axial angle $\theta_1 = \theta_{k2}$ and weak primary meridian axial angle $\theta_2 = \theta_{k1}$. Such obtained radii of curvature $r_1$ and $r_2$ and the axial angles $\theta_1$ and $\theta_2$ are memorized in the data memory 101.

In the single measuring mode, the calculation and control circuit portion 55 displays only the measured data obtained through the respective measuring modes in accordance with the program memory.

Although several embodiments have been described, there can be used the area CCD 18 of the anterior portion observing system 2 as the alignment sensor 32.

What is claimed is:

1. An ophthalmological instrument for the use of both corneal configuration and intraocular pressure measurement including:
   alignment watching means for watching an alignment completion state upon receipt of an alignment completion signal which is output by alignment detecting means for detecting the alignment of an apparatus body with respect to an eye to be tested;
   corneal configuration measuring means for projecting a ring target mark onto the cornea of the eye and measuring a corneal configuration with reference to said ring target image;
   noncontact type intraocular pressure measuring means for discharging fluid toward the cornea in order to transfigure the cornea and measuring the intraocular pressure with reference to the amount of such transfiguration; and
   automatic executing means for executing the corneal configuration and intraocular pressure measurements in such a manner as that data of the ring target image is intaken in accordance with output of said alignment watching means in order to obtain data regarding the corneal configuration and thereafter checking whether the alignment completion state is maintained and if affirmative, automatically starting a fluid discharge onto the cornea.

2. An ophthalmological instrument for the use of both corneal configuration and intraocular pressure measurement including:
   alignment detecting means for detecting the alignment of an apparatus body with respect to an eye to be tested;
   corneal configuration measuring means for automatically projecting a ring target mark of the cornea of the eye in accordance with an alignment completion output of said alignment completion detecting means and calculation means to measure the radius of curvature of the cornea with reference to the ring target image formed on the cornea;
   data check means for checking whether data regarding the radius of curvature of the cornea is obtained; and
   noncontact type intraocular pressure measuring means for discharging fluid toward the cornea in order to transfigure the cornea and measuring the intraocular pressure with reference to the amount of such transfiguration under the conditions that the alignment completion state is still maintained and that the data regarding the radius of curvature is obtained based on said data check means and said alignment detecting means.

3. An ophthalmological instrument including:
   an alignment detecting system for aligning an optical axis with the vertex of the cornea of an eye to be tested and detecting the amount of working distance;
   a noncontact type intraocular pressure measuring system;
   a corneal configuration measuring system for projecting a predetermined target mark onto the cornea of the eye, permitting a light receiving element to receive a kerato ring image of the target mark, and performing a calculation with reference to the configuration of the kerato ring image thereby to measure the radius of curvature of the cornea; and
   correcting means for performing correction with reference to the amount of the working distance which is detected by said alignment detecting system when the corneal configuration is being calculated by said corneal configuration measuring system.

* * * * *